US009113626B2

(12) United States Patent
Dairiki et al.

(10) Patent No.: US 9,113,626 B2
(45) Date of Patent: Aug. 25, 2015

(54) EMULSION COMPOSITION AND AGROCHEMICAL EMULSION COMPOSITION

(75) Inventors: Hiroshi Dairiki, Odawara (JP); Tetsutaro Kai, Haibara-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 723 days.

(21) Appl. No.: 12/734,566

(22) PCT Filed: Nov. 11, 2008

(86) PCT No.: PCT/JP2008/003250
§ 371 (c)(1),
(2), (4) Date: May 10, 2010

(87) PCT Pub. No.: WO2009/063608
PCT Pub. Date: May 22, 2009

(65) Prior Publication Data
US 2010/0234232 A1     Sep. 16, 2010

(30) Foreign Application Priority Data
Nov. 14, 2007   (JP) ................................ 2007-295688

(51) Int. Cl.
*A01N 59/08* (2006.01)
*A01N 35/10* (2006.01)
*A01P 7/04* (2006.01)
*A01P 3/00* (2006.01)
*A01P 13/00* (2006.01)
*A01N 25/04* (2006.01)
*B01F 17/00* (2006.01)

(52) U.S. Cl.
CPC ............ *A01N 25/04* (2013.01); *B01F 17/0085* (2013.01); *B01F 17/0092* (2013.01)

(58) Field of Classification Search
CPC ....... A01N 25/04; A01N 25/02; A01N 25/30; A01N 43/16; A01N 43/50; A01N 43/58; A01N 47/38
USPC ................. 424/678; 504/116.1, 343; 514/634
See application file for complete search history.

(56) References Cited

U.S. PATENT DOCUMENTS

| 4,125,393 A | 11/1978 | Kohl et al. |
| 6,620,421 B1 | 9/2003 | Nishi et al. |
| 2006/0035787 A1 | 2/2006 | Dairiki et al. |

FOREIGN PATENT DOCUMENTS

| EP | 2216092 A1 * | 8/2010 |
| JP | 50-157160 A | 12/1975 |
| JP | A-02-295903 | 12/1990 |
| JP | A-06-256122 | 9/1994 |
| JP | A-06-305915 | 11/1994 |
| JP | 07-003478 A | 1/1995 |
| JP | 09052810 A * | 2/1997 |
| JP | A-09-052810 | 2/1997 |
| JP | 09-272755 A | 10/1997 |
| JP | A-10-072305 | 3/1998 |
| JP | A-2000-239102 | 9/2000 |
| JP | A-2000-514793 | 11/2000 |
| JP | A-2001-172103 | 6/2001 |
| JP | A-2001-270801 | 10/2001 |
| JP | 2002-537312 A | 11/2002 |
| JP | A-2003-128501 | 5/2003 |
| JP | 2003-528935 A | 9/2003 |
| JP | 2003-534446 A | 11/2003 |
| JP | 2004-066121 A | 3/2004 |
| JP | 2006-501198 A | 1/2006 |
| JP | 201322433 A * | 10/2013 |
| JP | 5628979 B * | 11/2014 |
| WO | WO 94/23578 A1 | 10/1994 |
| WO | WO 98/00009 A1 | 1/1998 |
| WO | WO 99/00010 A1 | 1/1998 |
| WO | WO9800009 A1 * | 1/1998 |
| WO | WO 99/65300 A1 | 12/1999 |
| WO | WO 00/21915 A1 | 4/2000 |
| WO | WO 00/49873 A1 | 8/2000 |
| WO | WO 00/77088 A1 | 12/2000 |
| WO | WO 01/90286 A1 | 11/2001 |
| WO | WO 2004/009564 A1 | 1/2004 |
| WO | WO 2004/014136 A1 | 2/2004 |
| WO | WO 2004/077945 A1 | 9/2004 |
| WO | WO 2005/095380 A1 | 10/2005 |
| WO | WO 2007/040280 A1 | 4/2007 |
| WO | WO 2007/040282 A1 | 4/2007 |

OTHER PUBLICATIONS

International Search Report issued in International Application No. PCT/JP2008/003250 on Mar. 3, 2009 (with English-language translation).
Database WPI Week 199718, Thomson Scientific, London, GB; AN 1997-197186, XP002665901 & JP 9-052810 A, (Dainippon Ink & Chem. Inc) Feb. 25, 1997) Abstract.

* cited by examiner

*Primary Examiner* — Janet Epps-Smith
*Assistant Examiner* — Courtney Brown
(74) *Attorney, Agent, or Firm* — Foley & Lardner LLP

(57) ABSTRACT

This invention provides an emulsifiable concentrate composition, containing a component (A) which is at least one selected from the group consisting of alkanol having 6 to 20 carbon atoms, alkenol having 6 to 20 carbons, polyoxyethylene alkyl ester, polyoxyethylene alkyl diester, polyoxyethylene alkenyl ester, polyoxyethylene dialkenyl ester, polyoxyethylene•polyoxypropylene•block copolymer and a silicon-based surfactant, a component (B) which is at least one polyoxyalkylene aryl phenyl ether, and a component (C) which is an aromatic hydrocarbon-based nonpolar solvent, wherein the emulsifiable concentrate composition contains neither anionic surfactant nor cationic surfactant, and an agrochemical emulsifiable concentrate composition using the emulsifiable concentrate composition.

12 Claims, No Drawings

US 9,113,626 B2

EMULSION COMPOSITION AND AGROCHEMICAL EMULSION COMPOSITION

TECHNICAL FIELD

The present invention relates to an emulsifiable concentrate composition capable of preparing an agrochemical emulsifiable concentrate composition having good emulsifiability which is not affected by the ionicity of an agrochemical active ingredient to be used together with the emulsifiable concentrate composition, and an agrochemical emulsifiable concentrate composition containing the emulsifiable concentrate composition and an agrochemical active ingredient.

Priority is claimed on Japanese Patent Application No. 2007-295688, filed Nov. 14, 2007, the content of which is incorporated herein by reference.

BACKGROUND ART

Up until now, agrochemical active ingredients having a bactericidal activity, pesticidal activity, acaricidal activity, herbicidal activity or the like, have been used by formulating them into various easy-to-use shapes. In the case where the agrochemical active ingredient is lipophilic, the agrochemical active ingredient was used in such a manner that the agrochemical active ingredient was mixed with an emulsifiable concentrate composition to obtain an emulsion (agrochemical emulsifiable concentrate composition), then the resulting emulsion was diluted with water.

In general, an emulsifiable concentrate composition contains an organic solvent which is able to dissolve an agrochemical active ingredient and a surfactant which is an emulsifier. As for the surfactant, usually, an anionic surfactant having excellent emulsifiability has been used. However, if a cationic agrochemical active ingredient was used together with the resulting agrochemical emulsifiable concentrate composition to be diluted, the anionic surfactant and the cationic agrochemical active ingredient may form a salt, thereby causing flocculation.

Meanwhile, as for a surfactant other than the anionic surfactant, which has good emulsifiability, polyoxy alkylene aryl phenyl ether which is a nonionic surfactant has been known (Patent Documents 1 to 7). However, in order to attain sufficient emulsifiability, it was necessary to use a large amount of the surfactant even when using this surfactant.

In recent years, it has been required to use environmentally-friendly agricultural chemicals. For example, the United States Environmental Protection Agency (EPA) has restrictions on the content of polyoxy alkylene aryl phenyl ether contained in the emulsifiable concentrate composition.

[Patent Document 1] Japanese Unexamined Patent Application, First Publication No. H10-72305

[Patent Document 2] Japanese Unexamined Patent Application, First Publication No. 2000-239102

[Patent Document 3] Japanese Unexamined Patent Application, First Publication No. 2000-514793

[Patent Document 4] Japanese Unexamined Patent Application, First Publication No. 2003-128501

[Patent Document 5] Japanese Unexamined Patent Application, First Publication No. H6-305915

[Patent Document 6] Japanese Unexamined Patent Application, First Publication No. H9-52810

[Patent Document 7] Japanese Unexamined Patent Application, First Publication No. 2001-270801

DISCLOSURE OF INVENTION

Problems to be Solved by the Invention

The present invention was conceived in view of the above-described circumstances encountered in the conventional art, and has, as its objective, the provision of an emulsifiable concentrate composition which is environmentally-friendly and able to prepare an agrochemical emulsifiable concentrate composition having good emulsifiability, and an agrochemical emulsifiable concentrate composition containing the emulsifiable concentrate composition and an agrochemical active ingredient.

Means for Solving the Problems

In order to achieve the above objective, the inventors of the present invention conducted intensive investigations on an agrochemical emulsifiable concentrate composition which uses polyoxyalkyl aryl phenyl ether of a nonionic surfactant as a surfactant. As a result, the inventors of the present invention discovered that an emulsifiable concentrate composition containing a component (A): alkanol having 6 to 20 carbon atoms, a component (B): polyoxyalkylene aryl phenyl ether and a component (C): aromatic hydrocarbon-based nonpolar solvent, and an agrochemical emulsifiable concentrate composition using the emulsifiable concentrate composition, are environmentally-friendly and have good emulsifiability which is not affected by the ionicity of the agrochemical active ingredient to be used together with the emulsifiable concentrate composition. In doing so, the inventers achieved the present invention.

According to the first embodiment of the present invention, the following emulsifiable concentrate compositions (1) to (8) are provided.

(1) An emulsifiable concentrate composition, comprising a component (A) which is at least one selected from the group consisting of alkanol having 6 to 20 carbon atoms, alkenol having 6 to 20 carbons, polyoxyethylene alkyl ester, polyoxyethylene alkyl diester, polyoxyethylene alkenyl ester, polyoxyethylene dialkenyl ester, polyoxyethylene•polyoxypropylene•block copolymer and a silicon-based surfactant, a component (B) which is at least one polyoxyalkylene aryl phenyl ether, and a component (C) which is an aromatic hydrocarbon-based nonpolar solvent, wherein the emulsifiable concentrate composition contains neither anionic surfactant nor cationic surfactant.

(2) The emulsifiable concentrate composition according to (1), wherein the component (A) is at least one selected from the group consisting of lauryl alcohol, polyoxyethylene monolaurate, polyoxyethylene dilaurate, polyether-modified silicon oil.

(3) The emulsifiable concentrate composition according to (1) or (2), wherein the component (B) is a polyoxyethylene tristyryl phenyl ether.

(4) The emulsifiable concentrate composition according to any one of (1) to (3), wherein the component (C) is at least one selected from the group consisting of alkyl benzenes and naphthalenes.

(5) The emulsifiable concentrate composition according to any one of (1) to (4), further comprising a component (D) which is a polar solvent.

(6) The emulsifiable concentrate composition according to (5), wherein the component (D) is ketones or lactones.

(7) The emulsifiable concentrate composition according to (1), wherein the component (A) is lauryl alcohol, the component (B) is a polyoxyetylene tristyryl phenyl ether, the component (C) is at least one selected from the group consisting of alkylbenzenes and naphthalenes, and the component (D) is ketones or lactones.

(8) The emulsifiable concentrate composition according to any one of (1) to (7), wherein the content of the component (A) is 1 to 20% by weight, the content of the component (B) is 5 to 25% by weight, the content of the component (C) is 10 to 45% by weight, and the content of the component (D) is 0 to 75% by weight.

According to the second embodiment of the present invention, the following agrochemical emulsifiable concentrate compositions (9) to (10) can be provided.

(9) An agrochemical emulsifiable concentrate composition, comprising the emulsifiable concentrate composition according to any one of (1) to (8), and at least one agrochemical active ingredient.

(10) The agrochemical emulsifiable concentrate composition according to (9), wherein the content of the component (A) is 0.5 to 10% by weight, the content of the component (B) is 0.5 to 15% by weight, the content of the component (C) is 5 to 80% by weight, the content of the component (D) is 0 to 60% by weight, and the content of the agrochemical active ingredient is 1 to 80% by weight.

Effects of the Invention

Since the emulsifiable concentrate composition of the present invention contains neither anionic surfactant nor cationic surfactant, it makes it possible to prepare an agrochemical emulsifiable concentrate composition having good emulsifiability which is not affected by the ionicity of the agrochemical active ingredient to be used together with the emulsifiable concentrate composition.

Further, since it is not necessary to use a large amount of polyoxy alkylene aryl phenyl ether in the present invention, the emulsifiable concentrate composition of the present invention is environmentally-friendly.

Further, since the agrochemical emulsifiable concentrate composition of the present invention uses the emulsifiable concentrate composition of the present invention, the agrochemical emulsifiable concentrate composition of the present invention maintains good emulsifiability for a long time.

Further, the agrochemical emulsifiable concentrate composition of the present invention has good emulsifiability without causing flocculation, even in the case where an agrochemical active ingredient having the ionicity (cationicity) is used together with the emulsifiable concentrate composition.

BEST MODE FOR CARRYING OUT THE INVENTION

The present invention will now be explained below in detail.

1) Emulsifiable Concentrate Composition

The emulsifiable concentrate composition of the present invention contains a component (A) which is at least one selected from the group consisting of alkanol having 6 to 20 carbon atoms, alkenol having 6 to 20 carbons, polyoxyethylene alkyl ester, polyoxyethylene alkyl diester, polyoxyethylene alkenyl ester, polyoxyethylene dialkenyl ester, polyoxyethylene•polyoxypropylene•block copolymer and a silicon-based surfactant, a component (B) which is at least one polyoxyalkylene aryl phenyl ether, and a component (C) which is an aromatic hydrocarbon-based nonpolar solvent, wherein the emulsifiable concentrate composition contains neither anionic surfactant nor cationic surfactant.

Component (A):

The emulsifiable concentrate composition of the present invention contains at least one selected from the group consisting of alkanol having 6 to 20 carbon atoms, alkenol having 6 to 20 carbons, polyoxyethylene alkyl ester (hereafter, polyoxyethylene may be abbreviated to "POE"), POE alkyl diester, POE alkenyl ester, POE dialkenyl ester, polyoxyethylene•polyoxypropylene•block copolymer (hereafter, polyoxypropylene may be abbreviated to "POP") and a silicon-based surfactant as a component (A). By adding the component (A), the emulsifiability can be improved when the emulsifiable concentrate composition is diluted with water and the precipitation of the crystal of the agrochemical active ingredient in water can be prevented.

Examples of alkanol having 6 to 20 carbons include n-hexyl alcohol, n-octyl alcohol, 2-ethylhexyl alcohol, n-decyl alcohol, lauryl alcohol, myristyl alcohol, cetyl alcohol, stearyl alcohol and the like.

Examples of alkenol having 6 to 20 carbons include palmitoyl alcohol, oleyl alcohol, linoleyl alcohol and the like.

Examples of POE alkyl ester include POE monolaurate, POE monostearate and the like.

Examples of POE dialkyl ester include POE dilaurate, POE distearate and the like.

Examples of POE alkenyl ester include POE monooleate and the like.

Examples of POE dialkenyl ester include POE dioleate and the like.

Examples of POE•POP block polymer include a POE•POP•block polymer having molecular weight of 500 to 20000. Among these, POE•POP•block polymer having molecular weight of 1000 to 10000 is preferable. Further, the ratio of polyoxyethylene in the block polymer is preferably 5 to 70 mol %, and more preferably 10 to 40 mol %.

A silicon-based surfactant is a surfactant having silicon atoms in the molecule. Examples of the silicon-based surfactant include a nonionic surfactant containing a polyether-modified silicon oil as a main component. In the polyether-modified silicon oil, polyethylene oxide, polypropylene oxide or both of them are introduced to some of methyl groups bounded in the end or side-chain of methyl polysiloxane or dimethyl polysiloxane, and in some cases, hydroxyl group bounded in the end is etherified or esterified by alkyl group.

Examples of polyether-modified silicon oil include commercially available products, such as trade name: Sylgard series (manufactured by Dow Corning Silicone Co., Ltd.), Sylwet series (manufactured by Nippon Unicar Company Limited), Silicone oil KF series (manufacture by Shin-Etsu Chemical Co., Ltd.), Kinetic (manufactured by Helena Chemical Company) or the like.

These can be used alone, or in combinations of two or more.

Among these, alkanol having 6 to 20 carbons, POE alkyl ester, POE dialkyl ester or a silicon-based surfactant is preferable as the component (A), and lauryl alcohol, POE monolaurate, POE dilaurate or polyether-modified silicon-based oil is more preferable in terms of obtaining a composition having better emulsifiability.

Component (B):

The emulsifiable concentrate composition of the present invention contains at least one polyoxyalkylene aryl phenyl ether which is a nonionic surfactant as a component (B). By adding at least one polyoxyalkylene aryl phenyl ether which is a nonionic surfactant as the component (B), an agrochemical emulsifiable concentrate composition having good emulsifiability which is not affected by the ionicity of an agrochemical active ingredient to be used together with the emulsifiable concentrate composition can be prepared.

Examples of the moiety of polyoxyalkylene group in the polyoxyalkylene aryl phenyl ether include polyoxyethylene group, polyoxypropylene group, polyoxybutylene group and the like. The degree of polymerization of the polyoxylakylene moiety is usually 2 to 50, preferably 3 to 20, more preferably 4 to 15, and particularly preferably 5 to 10.

Examples of the moiety of aryl group include aryl group having 6 to 40 carbons, such as phenyl group, naphthyl group, styryl group or the like. Examples of the moiety of phenyl ether include mono-, di- or tri-substituted phenyl ether or the like.

Specific examples of polyoxyalkylene aryl phenyl ether include POE monostyryl phenyl ether, POE distyryl phenyl ether, POE tristyryl phenyl ether, polyoxypropylene tristyryl phenyl ether, POE polyoxy propylene tristyryl phenyl ether and the like.

These can be used alone or in combinations of two or more.

Among these, POE tristyryl phenyl ether is preferable in terms of obtaining a composition having better emulsifiability.

Component (C):

The emulsifiable concentrate composition of the present invention includes aromatic hydrocarbon-based nonpolar solvent as a component (C). The aromatic hydrocarbon-based nonpolar solvent is preferably at least one selected from the group consisting of alkylbenzenes and naphthalenes.

Examples of the alkylbenzenes include toluene, xylene, trimethyl benzene, cumene and the like. Examples of the naphthalenes include naphthalene, methylnaphthalene and the like.

These solvent can be used alone or in combinations of two or more.

It is also allowed to directly use a commercially available product as the component (C). Examples of the commercially available product include Solvesso 100, Solvesso 150, Solvesso 200 (Solvesso is a trade mark of Exxon Chemical Company) and the like.

Component (D):

The emulsifiable concentrate composition of the present invention preferably further includes a polar solvent as a component (D) when preparing an agrochemical emulsifiable concentrate composition containing an agrochemical active ingredient having a low solubility to aromatic hydrocarbon-based nonpolar solvent of the component (C).

Examples of the polar solvent include ketones, lactones, N-methyl-2-pyrrolidone, n-amyl acetate, propylene glycol monomethyl ether, propylene carbonate, lactic acid butyl ester, lactic acid ethyl ester, isobornyl acetate, tetrahydrofurfuryl alcohol, 3-methoxy-3-methyl-1-butanol, sulfolane, D-limonene and the like.

Among these, ketones and lactones are preferable, and γ-butyrolactone is more preferable in terms of obtaining a composition having better emulsifiability.

Examples of ketones include acetone, methyl ethyl ketone, diethyl ketone, methyl isobutyl ketone, methyl-n-amyl ketone (2-heptanone), mesityl oxide, cyclopentanone, cyclohexanone and the like.

Examples of lactones include γ-butyrolatone, δ-lactone and the like.

These polar solvants can be used alone or in combination of two or more.

The ratio of each component in the emulsifiable concentrate composition of the present invention is not particularly limited, although the content of the component (A) is usually 1 to 20% by weight, preferably 2 to 15% by weight, the content of the component (B) is usually 5 to 25% by weight, preferably 10 to 18% by weight, the content of the component (C) is usually 10 to 45% by weight, preferably 15 to 35% by weight, the content of the component (D) is usually 0 to 75% by weight, preferably 30 to 70% by weight.

Since it is not necessary to use a large amount of polyoxyalkylene aryl phenyl ether which is the component (B), the emulsifiable concentrate composition of the present invention is environmentally-friendly.

Other organic solvents may be added to the emulsifiable concentrate composition of the present invention as long as the organic solvents do not undermine the effects of the present invention.

Examples of other solvents include phthalate esters, vegetable oil, and the like.

Furthermore, an additive, such as an ultraviolet absorbing agent, an antioxidant, an antiseptic agent, an efficiency-enhancing agent, a coloring agent, perfume or the like may be added to the emulsifiable concentrate composition of the present invention as long as the additive does not undermine the effects of the present invention.

The emulsifiable concentrate composition of the present invention can be prepared by well-known preparation methods. For example, the emulsifiable concentrate composition can be prepared by mixing and agitating a predetermined amount of the components (A) to (C), if necessary, the component (D) and/or other components. The order of adding-mixing the components is not limited.

2) Agrochemical Emulsifiable Concentrate Composition

The agrochemical emulsifiable concentrate composition of the present invention contains the above-described emulsifiable concentrate composition of the present invention and at least one agrochemical active ingredient.

The agrochemical active ingredient is not limited, although it may be in liquid form or solid form, or it may be an organic compound or an inorganic compound, or it may be a single compound or a mixture.

Examples of the agrochemical active ingredient include fungicides, pesticides, miticides, herbicides, antibacterial agents, antifungal agents, anti-mold agents, algicide, plant growth regulators, rodenticides, and the like shown below may be cited. These agrochemical active ingredients may be used alone or in combinations of two or more.

Examples of fungicides which may be cited include CNA, DPC, EDDP, IBP, PCNB, TPN, *agrobacterium*, isoprothiolane, ipconazole, iprodione, imibenconazole, echlomezole, oxadixyl, oxycarboxin, oxytetracycline, oxolinic acid, kasugamycin, carbendazole, quinoxaline, captan, chloroneb, diethofencarb, dicromezine, dithianon, zineb, difenoconazole, cyproconazole, dimethirimol, ziram, sulfenic acid-based (dichlofluanid), dazomet, thiadiazine, thiabendazole, thiophanate methyl, tiliadin, tecloftalam, tebuconazole, triadimefon, triazine, trichlamide, tricyclazole, triflumizole, triforine, triclofos methyl, validamycin, bitertanol, hydroxy-isoxazole, pyrazophos, pyrifenox, pyroquilon, vinclozolin, fenarimol, ferimzone, fthalide, blasticidin, fluazinam, fluoroimide, flusulfamide, flutolanil, prochloraz, procymidone, propiconazole, propineb, probenazole, hexaconazole, pefurazoate, pencycuron, benthiazole, fosetyl, polyoxin, polycarbamate, myclobutanil, mildiomycin, methasulfocarb, metalaxyl, mepanipyrim, mepronil, and the like.

Examples of insecticides which may be cited include BPMC, BPPS, BRP, CPCBS, CVMP, CVP, CYAP, DCIP, DEP, ECP, EPN, ESP, MIPC, MPMC, MPP, MTMC, PAP, PHC, PMP, XMC, acrinathrin, acetamiprid, acephate, amitraz, alanycarb, allethrin, isoxathion, isophenphos, imidacloprid, ethiofencarb, ethion, ethylthiometon, ethofenprox, ethoprophos, etrimfos, oxamyl, sodium oleate, carbosulfan, quinalphos, clothianidin, chlorfentezine, chlorpyrifos, chlorpyrifos-methyl, chlorfluazuron, chlorobenzilate, kelthane, salithion, dienochlor, cycloprothrin, dinotefuran, cyhalothrin, cyfluthrin, diflubenzuron, cypermethrin, dimethylvinphos, dimethoate, cyromazine, sulprofos, diazinon, thiachloprid, thiamethoxam, thiodicarb, thiometon, tetradifon, tebufenpyrad, tefluthrin, teflubenzuron, tralomethrin, nitenpyram, vamidothion, halfenprox, bifenthrin, pryaclofos, pyridaphenthion, pyridaben, pirimicarb, pyrimidifen, pirimiphos-methyl, fipronil, fenisobromolate, fenoxycarb, fenothiocarb, fenvalerate, fenpyroximate, fenpropathrin, buprofezin, furathiocarb, flucythrinate, prothiofos, propafos, profenofos, hexythiazox, permethrin, bensultap, benzoepin, benzomate, bendiocarb, benfuracarb, phosalone, fosthiazate, polybutene, formothion, malathion, mesulfenfos, methomyl, metaldehyde, monocrotophos, resmethrin, and the like.

Examples of herbicides which may be cited include 2,4-PA, ACN, CNP, DAP, DBN, DCBN, DCMU, DCPA, DPA, DSMA, IPC, MBPMC, MCC, MCP, MCPB, MCPP, MDBA, PAC, SAP, TCA, TCTP, ioxynil, asulam, atrazine, amiprophosmethyl, ametrine, alachlor, alloxydim, isouron, isoxaben, imazapyr, imazosulfuron, esprocarb, ethidimuron, oxadiazon, orthobencarb, karbutilate, quizalofop ethyl, quinclorac, glyphosate, chlormetoxinyl, clomeprop, chlorphthalim, cyanazine, dithiopyr, siduron, cinosulfuron, diphenamide, simazine, dimethametryn, simetryn, dimepiperate, terbacil, daimuron, thiazafluron, thifensulfuron-methyl, tetrapion, thenylchlor, tebuthiuron, triclopyr, trifluralin, naproanilide, napropamide, bialaphos, picloram, bifenox, piperophos, pyrazoxyfen, pyrazosulfuron ethyl, pyrazolate, pyributycarb, fenoxaprop ethyl, phenothiol, phenmedipham, butachlor, butamifos, flazasulfuron, fluazifop, pretilachlor, prodiamine, propyzamide, bromacil, prometryn, bromobutide, hexadinone, bethrodine, bensulfuron methyl, benzophenap, bentazone, benthiocarb, pendimethalin, fosamine ammonium, methyl daimuron, metsulfuron methyl, metolachlor, metribuzine, mefenaset, molinate, linuron, lenacil, and the like.

Examples of antibacterial agents, antifungal agents and anti-mold agents which may be cited include trialkyl triamine, ethanol, isopropyl alcohol, propyl alcohol, trisnitro, chlorobutanol, pronopol, glutaraldehyde, formaldehyde, α-bromocinnamaldehyde, Skane M-8, Kathon CG, NS-500W, BIT, n-butyl BIT, allyl isothiocyanate, thiabendazole, methyl 2-benzimidazolyl carbamate, lauricidin, BioBang, triclocarban, halocarban, glasisicar, benzoic acid, sorbic acid, caprylic acid, propionic acid, 10-undecylenic acid, potassium sorbate, potassium benzoate, monomagnesium phthalate, 8-hydroxyquinoline, TMTD, triclosan, dichlofluanilide, tolyfluanid, milt protein, egg white lysozyme, benthiazole, carbam-sodium, triazine, tebuconazole, hinokitiol, tetrachloroisophthalonitrile, tectamer 38, chlorhexidine gluconate, polyhexamethylene biguanide, danthoprom, clidant, sodium pyrithione, zinc pyrithione, densill, thymol, isopropyl methyl phenol, OPP, phenol, butyl paraben, ethyl paraben, methyl paraben, propyl paraben, metacresol, orthocresol, paracresol, sodium ortho-phenyl phenol, chlorophen, p-chlorophenol, parachloromethaxylate, parachlorocresol, fluor folpet, polylysine, Biopan P-1487, Jote methyl-paratolylsulfone, polyvinylpyrrolidone parachloroisocyanel, Novalon AG300, Holon Killer, Dimer 136, benzalkonium chloride, didecyl dimethyl ammonium chloride, Bardac 2250/80, benzotonium chloride, Hyamine 3500J, cetyl ammonium bromide, cetrimide, CTAB, cetavlon, Dimer 38, benzalkonium chloride, Hyamine 3500J Bardac 170P, DC-5700, cetylpyridinium chloride, diuron, DCMU, Prepentol A6, CMI, 2CI-OIT, BCM, ZPT, BNP, OTT, IPBC, TCMSP, and the like.

Examples of plant growth regulators which may be cited include abscisic acid, inabenfide, indole butyric acid, uniconazole, ethychlozate, ethephon, oxyethylene docosanol, quinoxaline, DEP, cloxyfonac, chlormequat, chlorella extract, cyanamide, dichlorprop, gibberellin daminozide, decylalcohol, trinexapac-ethyl, paclobutrazol, paraffin, piperonyl butoxide, pyraflufen-ethyl, flurprimidol, prohydrojasmon, prohexadione-calcium, benzylaminopurine, pendimethalin, benfuracarb, inabenfide forchlorfenuron, potassium maleic hydrazide, 1-naphthylacetamide, 4-CPA, MCPA thioethyl, MCPB and the like.

Examples of rodenticides which may be cited include coumarin-based rodenticides, chlorophacinone and the like.

Furthermore, acaricidal active ingredients described in WO2005/095380, WO2007/040280, WO2007/040282 and the like may be used as the agrochemical active ingredient of the present invention. The specific examples of the agrochemical active ingredient may be represented by the formula (i) below.

[Chemical formula 1]

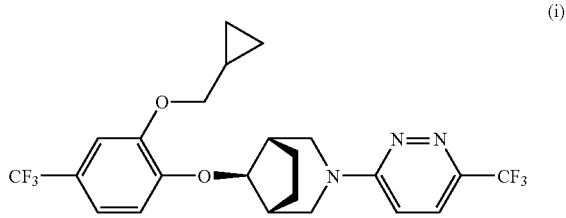

(i)

The ratio of each component in the agrochemical emulsifiable concentrate composition of the present invention is not particularly limited, although the content of the component (A) is usually 0.5 to 15% by weight, preferably 1 to 10% by weight, the content of the component (B) is usually 0.5 to 15% by weight, preferably 1 to 15% by weight, the content of the component (C) is usually 5 to 80% by weight, preferably 10 to 30% by weight, the content of the component (D) is usually 0 to 60% by weight, preferably 5 to 55% by weight, and the content of the agrochemical active ingredient is usually 1 to 80% by weight, preferably 5 to 20% by weight.

The agrochemical emulsifiable concentrate composition of the present invention can be prepared by well-known preparation methods. For example, (i) a preparation method of mixing and agitating a predetermined amount of the emulsifiable concentrate composition of the present invention and an agrochemical active ingredient, (ii) a preparation method of mixing and agitating the components (A) to (C), if necessary, the component (D), and an agrochemical active ingredient. The order of adding-mixing those components is not limited in the methods.

The agrochemical emulsifiable concentrate composition of the present invention maintains good emulsifiability for a long time, since it contains the emulsifiable concentrate composition of the present invention.

Since the agrochemical emulsifiable concentrate composition of the present invention contains an emulsifiable concentrate composition which does not contain anionic surfactant, the agrochemical emulsifiable concentrate composition has good emulsifiability without causing flocculation even in the case where an agrochemical active ingredient having the ionicity (cationicity) is used together with the emulsifiable concentrate composition.

The cationic agrochemical active ingredient which may be used in the present invention is not particularly limited, although examples of the cationic agrochemical active ingredient include iminoctadien albesilate, iminoctadien acetate, emamectin benzoate, oxine sulfate, oxpoconazole fumarate, cartap, chlormequat, choline, diquat, streptomycin, propamocarb hydrochloride, mepiquat chloride, monofluoroacetate, levamysol hydrochloride, paraquat, morantel tartrate; inorganic salts (plant growth regulator) such as calcium chloride, calcium sulfate, calcium peroxide; and the like.

Furthermore, the agrochemical emulsifiable concentrate composition of the present invention has good emulsifiability even in the case where an inorganic copper agent is used together with the agrochemical emulsifiable concentrate composition. Examples of the inorganic copper agent include antibacterial compounds including copper ions.

More specifically, examples of the inorganic copper agent include basic copper chloride, basic copper sulfate, basic copper carbonate, copper (I) oxide, basic copper phosphate, basic copper sulfate calcium, copper ammonium complex salt and the like. Among these, basic copper chloride and/or basic copper sulfate are preferable. The form of basic copper sulfate is not particularly limited, although the form of Bordeaux mixture can be cited as an example.

EXAMPLES

Examples will now be cited to explain the present invention more specifically. However, the present invention is not limited in any way by the following examples. In addition, the word "parts" indicates "parts by weight".

Example 1

12.3 parts of the compound represented by the above described formula (i), employed as an agrochemical active ingredient, was dissolved in a mixture of 23 parts of the component (C): Solvesso-200ND (trade mark of Exxon Mobil Company) and 45.9 parts of the component (D): cyclohexanone to obtain a mixture, and 15 parts of the component (B): POE tristyryl phenyl ether (HLB=11.8) and 3.8 parts of the component (A): lauryl alcohol were mixed and dissolved in the resulting mixture to obtain an agrochemical emulsifiable concentrate composition 1.

Example 2

With the exception of replacing 45.9 parts of cyclohexanone employed as the component (D) with 39.7 parts of cyclohexanone, and replacing 3.8 parts of laurylalcohol employed as the component (A) with 10 parts of POE oleic ester (HLB=7.7) in Example 1, an agrochemical emulsifiable concentrate composition 2 was obtained in the same manner as Example 1.

Example 3

With the exception of replacing 45.9 parts of cyclohexanone employed as the component (D) with 39.7 parts of cyclohexanone, and replacing 3.8 parts of laurylalcohol employed as the component (A) with 10 parts of modified silicon active agent in Example 1, an agrochemical composition 3 was obtained in the same manner as Example 1.

Example 4

With the exception of replacing 45.9 parts of cyclohexanone employed as the component (D) with 44.7 parts of cyclohexanone, and replacing 3.8 parts of laurylalcohol employed as the component (A) with 5 parts of laurylalcohol in Example 1, an agrochemical emulsifiable concentrate composition 4 was obtained in the same manner as Example 1.

Example 5

With the exception of replacing 12.3 parts of the component (i) with 12.3 parts of triflumizole (manufactured by NIPPON SODA CO., LTD.), an agrochemical emulsifiable concentrate composition 5 was obtained in the same manner as Example 1.

Example 6

With the exception of replacing 12.3 parts of the component (i) with 12.3 parts of hexythiazox (manufactured by NIPPON SODA CO., LTD.), an agrochemical emulsifiable concentrate composition 6 was obtained in the same manner as Example 1.

Example 7

With the exception of replacing 12.3 parts of the component (i) with 12.3 parts of tepraloxydim (manufactured by NIPPON SODA CO., LTD.), an agrochemical emulsifiable concentrate composition 7 was obtained in the same manner as Example 1.

Example 8

With the exception of replacing 45.9 parts of cyclohexanone employed as the component (D) with 39.7 parts of cyclohexanone, and replacing 3.8 parts of laurylalcohol employed as the component (A) with 10 parts of POE•POP block polymer (PluronicPE6100, trade mark of BASF Japan) in Example 1, an agrochemical emulsifiable concentrate composition 8 was obtained in the same manner as Example 1.

Comparative Example 1

With the exception of replacing 3.8 parts of laurylalcohol employed as the component (A) with 3.8 parts of dodecylbenzenesulfonic acid calcium salt in Example 1, an agrochemical emulsifiable concentrate composition 9 was obtained in the same manner as Example 1.

Comparative Example 2

With the exception of replacing 15 parts of POE tristyryl phenyl ether (HLB=11.8) employed as the component (B) with 15 parts of POE oleic ester (HLB=7.7) in Example 4, an agrochemical emulsifiable concentrate composition 10 was obtained in the same manner as Example 4.

Comparative Example 3

With the exception of replacing 15 parts of POE tristyryl phenyl ether (HLB=11.8) employed as the component (B) with 15 parts of POE sorbitan trioleate (HLB=11.4) in Example 4, an agrochemical emulsifiable concentrate composition 11 was obtained in the same manner as Example 4.

Comparative Example 4

With the exception of replacing 15 parts of POE tristyryl phenyl ether (HLB=11.8) employed as the component (B)

with 15 parts of POE castor oil ether (HLB=11.2) in Example 4, an agrochemical emulsifiable concentrate composition 12 was obtained in the same manner as Example 4.

The compositions of the agrochemical emulsifiable concentrate compositions of Examples 1 to 8 and Comparative Examples 1 to 4 are shown in Table 1. In addition, the unit of the values in the tables is parts by weight.

triflumizole, hexythiazox and tepraloxydim, the same results were obtained.

Meanwhile, in Comparative Examples 2 to 4, in which the component (B) was not used, good emulsifiability was not obtained except to the agrochemical emulsifiable concentrate composition of Comparative Example 3 obtained right after the dilution.

TABLE 1

| | Component | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 | Comp. Ex. 4 |
|---|---|---|---|---|---|---|---|---|---|---|---|---|---|
| Component (A) | Laurylalcohol | 3.8 | — | — | 5 | 3.8 | 3.8 | 3.8 | — | — | 5 | 5 | 5 |
| | POE oleic ester | — | 10 | — | — | — | — | — | — | — | 15 | — | — |
| | Modified silicon active agent | — | — | 10 | — | — | — | — | — | — | — | — | — |
| | POE•POP block polymer | — | — | — | — | — | — | — | 10 | — | — | — | — |
| Component (B) | POE tristyryl phenyl ether | 15 | 15 | 15 | 15 | 15 | 15 | 15 | 15 | 15 | — | — | — |
| Component (C) | Solvesso-200ND | 23 | 23 | 23 | 23 | 23 | 23 | 23 | 23 | 23 | 23 | 23 | 23 |
| Component (D) | Cyclohexanone | 45.9 | 39.7 | 39.7 | 44.7 | 45.9 | 45.9 | 45.9 | 39.7 | 45.9 | 44.7 | 44.7 | 44.7 |
| Agrochemical active ingredient | Compound (i) | 12.3 | 12.3 | 12.3 | 12.3 | — | — | — | 12.3 | 12.3 | 12.3 | 12.3 | 12.3 |
| | Triflumzole | — | — | — | — | 12.3 | — | — | — | — | — | — | — |
| | Hexythiazox | — | — | — | — | — | 12.3 | — | — | — | — | — | — |
| | Tepraloxydim | — | — | — | — | — | — | 12.3 | — | — | — | — | — |
| Other component | Dodecylbenzenesulfonic acid calcium salt | — | — | — | — | — | — | — | — | 3.8 | — | — | — |
| | POE sorbitan trioleate | — | — | — | — | — | — | — | — | — | — | 15 | — |
| | POE Castor oil ether | — | — | — | — | — | — | — | — | — | — | — | 15 |

Test Example 1

The emulsifiability of the agrochemical emulsifiable concentrate compositions 1 to 8 and 10 to 12 obtained in Examples 1 to 8 and Comparative Examples 2 to 4 was investigated when the agrochemical emulsifiable concentrate compositions were diluted 1,000 times with tap water. Further, the emulsion stability was investigated after statically placing the diluted solution in a constant temperature water tank at 5° C. for 1 day. In this test example, the emulsifiability and emulsion stability were visually examined in a comprehensive manner according to the existence or nonexistence of a crystal substance and deposit in the diluted solution. The results are shown in Table 2.

TABLE 2

| | Emulsifiability (right after dilution) | Emulsion stability (after placing 1 day at 5° C.) |
|---|---|---|
| Example 1 | Good | Good |
| Example 2 | Good | Good |
| Example 3 | Good | Good |
| Example 4 | Good | Good |
| Example 5 | Good | Good |
| Example 6 | Good | Good |
| Example 7 | Good | Good |
| Example 8 | Good | Good |
| Comp. Example 2 | unemulsified | Causes precipitation of crystal substance |
| Comp. Example 3 | Good | Causes precipitation of crystal substance |
| Comp. Example 4 | Emulsion particle is coarse | Causes precipitation of crystal substance |

As shown in Table 2, in Examples 1 to 4 and 8, in which the compound (i) was used as an agrochemical active ingredient, the agrochemical emulsifiable concentrate compositions showed good emulsifiability both right after the dilution and after placing them at 5° C. for 1 day. Furthermore, in Examples 5 to 7, in which the compound (i) was replaced with Test Example 2

The agrochemical emulsifiable concentrate compositions 1 and 9 each obtained in Example 1 and Comparative Example 1 respectively was diluted 500 times and 1,000 times respectively with hard water having hardness of 3 degrees to obtain a diluted solution (a), a diluted solution (b), a diluted solution (e) and a diluted solution (f).

BEFRAN Liquid 25 (effective ingredient iminoctadine acetate, trade mark of NIPPON SODA CO., LTD.) was added to the diluted solutions (a), (b), (e) and (f) so as to dilute it 2,000 times respectively to obtain a diluted solution (c), a diluted solution (d), a diluted solution (g) and a diluted solution (h). The resulting diluted solutions (c), (d), (g) and (h) were statically placed in a constant temperature water tank at 20° C. for 1 day, and the emulsifiability of the diluted solutions were investigated.

Furthermore, a diluted solution (i) was obtained by diluting BEFRAN Liquid 25 2,000 times with hard water having hardness of 3 degrees. Then the agrochemical emulsifiable concentrate compositions 1 and 9 were diluted 500 times and 1,000 times respectively by adding each of the agrochemical emulsifiable concentrate compositions 1 and 9 to the diluted solution (i) to obtain diluted solutions (j) to (m). The diluted solutions (j) to (m) were statically placed in a constant temperature water tank at 20° C. for 1 day, and the emulsifiability was investigated.

In this test example, the emulsifiability and emulsion stability were visually examined in a comprehensive manner according to the existence or nonexistence of a crystal substance and deposit in the diluted solution. The results were shown in Tables 3 and 4.

In addition, in the tables, "o" represents the result in which the agrochemical emulsifiable concentrate composition shows good emulsifiability, "x" represents the result in which flocculation occurs.

TABLE 3

| Diluted solution | Agrochemical emulsifiable concentrate composition (dilution rate) | BEFRAN Liquid 25 (dilution rate) | Emulsifiability |
|---|---|---|---|
| (a) | 1 (500) | — | o |
| (b) | 1 (1000) | — | o |
| (c) | 1 (500) | 2000 | o |
| (d) | 1 (1000) | 2000 | o |
| (e) | 9 (500) | — | o |
| (f) | 9 (1000) | — | o |
| (g) | 9 (500) | 2000 | x |
| (h) | 9 (1000) | 2000 | x |

TABLE 4

| Diluted solution | BEFRAN Liquid 25 (dilution rate) | Agrochemical emulsifiable concentrate composition (dilution rate) | Emulsifiability |
|---|---|---|---|
| (j) | 2000 | 1 (500) | o |
| (k) | 2000 | 1 (1000) | o |
| (l) | 2000 | 9 (500) | x |
| (m) | 2000 | 9 (1000) | x |

The results shown in Tables 3 and 4 shows that the agrochemical emulsifiable concentrate composition obtained in Example 1 has good emulsifiability even when BEFRAN Liquid 25 was used together with the composition in spite of the diluting order. Meanwhile, in the composition obtained in Comparative Example 1, flocculation was caused within one day.

Test Example 3

The agrochemical emulsifiable concentrate compositions 1, 2 and 9 each obtained in Examples 1 to 2 and Comparative Example 1 respectively were diluted 500 times and 1,000 times with hard water having hardness of 3 degrees to obtain diluted solutions (1), (2), (5), (6), (9) and (10).

CALKLON (effective ingredient: calcium chloride, trade mark of NIPPON SODA CO., LTD.) was added to the diluted solutions (1), (2), (5), (6), (9) and (10) respectively so as to dilute it 500 times to obtain diluted solutions (3), (4), (7), (8), (11) and (12). The diluted solutions (3), (4), (7), (8), (11) and (12) were statically placed in a constant temperature water tank at 20° C. for 1 day, and the emulsifiability of the diluted solutions was investigated. The results are shown in Table 5. In Table 5, "o" represents the result in which the agrochemical emulsifiable concentrate composition shows good emulsifiability, "x" represents the result in which sediments in the form of oil were deposited and flocculation occurs.

Furthermore, a diluted solution was obtained by diluting CALKLON 500 times with hard water having hardness of 3 degrees. The agrochemical emulsifiable concentrate compositions 1, 2 and 9 were added to the resulting diluted solution so as to dilute them 500 times and 1,000 times to obtain diluted solutions (13) to (18). The diluted solutions (13) to (18) were statically placed in a constant temperature water tank at 20° C. for 1 day, and the emulsifiability was examined. The results were shown in Table 6.

In Table 6, "o" represents the result in which the agrochemical emulsifiable concentrate composition shows good emulsifiability, and "x" represents the result in which sediments in the form of oil were deposited and flocculation occurs.

TABLE 5

| Diluted solution | Agrochemical emulsifiable concentrate composition (dilution rate) | CALKLON (dilution rate) | Emulsifiability |
|---|---|---|---|
| (1) | 1 (500) | — | o |
| (2) | 1 (1000) | — | o |
| (3) | 1 (500) | 500 | o |
| (4) | 1 (1000) | 500 | o |
| (5) | 2 (500) | — | o |
| (6) | 2 (1000) | — | o |
| (7) | 2 (500) | 500 | o |
| (8) | 2 (1000) | 500 | o |
| (9) | 9 (500) | — | o |
| (10) | 9 (1000) | — | o |
| (11) | 9 (500) | 500 | x |
| (12) | 9 (1000) | 500 | x |

TABLE 6

| Diluted Solution | CALKLON (dilution rate) | Agrochemical emulsifiable concentrate composition (dilution rate) | Emulsifiability |
|---|---|---|---|
| (13) | 500 | 1 (500) | o |
| (14) | 500 | 1 (1000) | o |
| (15) | 500 | 2 (500) | o |
| (16) | 500 | 2 (1000) | o |
| (17) | 500 | 9 (500) | x |
| (18) | 500 | 9 (1000) | x |

The results shown in Tables 5 and 6 show that the agrochemical emulsifiable concentrate compositions 1 and 2 obtained in Examples 1 and 2 have good emulsifiability even when CALKLON was used together with the compositions in spite of the diluting order.

Meanwhile, in the agrochemical emulsifiable concentrate composition 9 obtained in Comparative Example 1, sediments in the form of oil were deposited and flocculation occurred within 1 day.

INDUSTRIAL APPLICABILITY

Since the emulsifiable concentrate composition of the present invention contains neither anionic surfactant nor cationic surfactant, it makes it possible to prepare an agrochemical emulsifiable concentrate composition having good emulsifiability which is not affected by the ionicity of an agrochemical active ingredient to be used together with the emulsion. Further, since it is not necessary to use a large amount of polyoxy alkylene aryl phenyl ether, the emulsifiable concentrate composition of the present invention is environmentally-friendly.

Further, since the agrochemical emulsifiable concentrate composition of the present invention uses the emulsifiable concentrate composition of the present invention, the agrochemical emulsifiable concentrate composition of the present invention maintains good emulsifiability for a long time, and even in the case where an agrochemical active ingredient having an ionicity (cationicity) is used together with the emulsifiable concentrate composition, it has good emulsifiability without causing flocculation. Therefore, the present invention has industrial benefits.

The invention claimed is:
1. An emulsifiable concentrate composition, comprising
   a component (A) which is at least one selected from the group consisting of lauryl alcohol, polyoxyethylene monolaurate, polyoxyethylene dilaurate, and polyether-modified silicon oil, a component (B) which is a polyoxyethylene tristyryl phenyl ether, a component (C) which is an aromatic hydrocarbon-based nonpolar solvent, and a component (D) which is a polar solvent, wherein the emulsifiable concentrate composition contains neither anionic surfactant nor cationic surfactant, the component (D) is ketones or lactones, and the content of the component (D) is 30 to 70% by weight.

2. The emulsifiable concentrate composition according to claim 1, wherein the component (C) is at least one selected from the group consisting of alkyl benzenes and naphthalenes.

3. The emulsifiable concentrate composition according to claim 1, wherein the component (A) is lauryl alcohol, the component (B) is a polyoxyethylene tristyryl phenyl ether, the component (C) is at least one selected from the group consisting of alkylbenzenes and naphthalenes, and the component (D) is ketones or lactones.

4. The emulsifiable concentrate composition according to claim 1, wherein the content of the component (A) is 1 to 20% by weight, the content of the component (B) is 5 to 25% by weight, the content of the component (C) is 10 to 45% by weight, and the content of the component (D) is 30 to 70% by weight.

5. An agrochemical emulsifiable concentrate composition, comprising the emulsifiable concentrate composition according to claim 1, and at least one agrochemical active ingredient.

6. The agrochemical emulsifiable concentrate composition according to claim 5, wherein the content of the component (A) is 0.5 to 10% by weight, the content of the component (B) is 0.5 to 15% by weight, the content of the component (C) is 5 to 80% by weight, the content of the component (D) is 5 to 55% by weight, and the content of the agrochemical active ingredient is 1 to 80% by weight.

7. An agrochemical emulsifiable concentrate composition, comprising the emulsifiable concentrate composition according to claim 2, and at least one agrochemical active ingredient.

8. An agrochemical emulsifiable concentrate composition, comprising the emulsifiable concentrate composition according to claim 3, and at least one agrochemical active ingredient.

9. An agrochemical emulsifiable concentrate composition, comprising the emulsifiable concentrate composition according to claim 4, and at least one agrochemical active ingredient.

10. The agrochemical emulsifiable concentrate composition according to claim 7, wherein the content of the component (A) is 0.5 to 10% by weight, the content of the component (B) is 0.5 to 15% by weight, the content of the component (C) is 5 to 80% by weight, the content of the component (D) is 5 to 55% by weight, and the content of the agrochemical active ingredient is 1 to 80% by weight.

11. The agrochemical emulsifiable concentrate composition according to claim 8, wherein the content of the component (A) is 0.5 to 10% by weight, the content of the component (B) is 0.5 to 15% by weight, the content of the component (C) is 5 to 80% by weight, the content of the component (D) is 5 to 55% by weight, and the content of the agrochemical active ingredient is 1 to 80% by weight.

12. The agrochemical emulsifiable concentrate composition according to claim 9, wherein the content of the component (A) is 0.5 to 10% by weight, the content of the component (B) is 0.5 to 15% by weight, the content of the component (C) is 5 to 80% by weight, the content of the component (D) is 5 to 55% by weight, and the content of the agrochemical active ingredient is 1 to 80% by weight.

* * * * *